United States Patent [19]
Palkovich et al.

[11] Patent Number: 5,779,637
[45] Date of Patent: Jul. 14, 1998

[54] MAGNETIC RESONANCE IMAGING SYSTEM INCLUDING AN IMAGE ACQUISITION APPARATUS ROTATOR

[75] Inventors: Alex Palkovich, Oxford; John Bird, Oxon, both of England

[73] Assignee: Elscint, Ltd., Haifa, Israel

[21] Appl. No.: 642,435

[22] Filed: May 3, 1996

[30] Foreign Application Priority Data

May 11, 1995 [GB] United Kingdom ............... 9509911

[51] Int. Cl.⁶ ........................................... A61B 5/055
[52] U.S. Cl. .................................. 600/415; 324/318
[58] Field of Search ..................... 128/653.1, 653.2, 128/653.5; 5/601, 607; 324/318, 322; 600/410, 415

[56] References Cited

U.S. PATENT DOCUMENTS

| 4,651,099 | 3/1987 | Vinegar et al. ............... 128/653.5 |
| 4,875,485 | 10/1989 | Matsutani ................... 128/653.5 |
| 5,486,700 | 1/1996 | Silberklang et al. . |
| 5,519,372 | 5/1996 | Palkovich et al. . |

FOREIGN PATENT DOCUMENTS 3909276  10/1989  Germany ............... 128/653.5

Primary Examiner—Ruth S. Smith
Attorney, Agent, or Firm—Fenster & Company

[57] ABSTRACT

This invention is concerned with magnetic resonance imaging (MR) systems and more particularly with special MRI systems which enable rotating the data acquisition apparatus of the MRI system. Such systems enables imaging different body parts at a variety of angles; thus providing better diagnostic possibilities.

7 Claims, 2 Drawing Sheets

MAGNETIC RESONANCE IMAGING SYSTEM INCLUDING AN IMAGE ACQUISITION APPARATUS ROTATOR

FIELD OF INVENTION

This invention is concerned with magnetic resonance imaging (MRI) systems and more particularly with such systems wherein the position of the subject is adjustable.

BACKGROUND OF THE INVENTION

MRI systems are used today for diagnosis a large variety of body parts such as brain. spine. heart knees. stomach and kidneys. These systems are based on nuclear phenomena which occurs when atomic nuclei ("spins") located in a static/ uniform magnetic field, are stimulated by a second magnetic field rotating at the Larmor frequency associated with particular nuclei. Upon removal of the rotating stimulation field, the stimulated nuclei relax and emit the absorbed energy in the form of radio frequency signals termed NMR signals, which are received and processed to provide a visible display of the nuclei.

In a typical MRI system the patient is positioned on a special horizontal bed while the image acquisition process is in progress. It has been pointed out by physician that many organs and functions of the body, when imaged by MRI systems, have different parameters in the prone and standing positions.

Therefore, using an MRI system which can acquire data by imaging a specific organ when the patient is in both a prone and in a standing positions would be highly beneficial. For example, by imaging the spine in different postures ranging from the horizontal to the vertical, more information about problems in the spine would be detected. One could more easily diagnose problems associated with the relative position of two consecutive vertebras, by comparing two images of the spine in two different positions: in the prone position and under stress, i.e., when a person is standing up.

No known available MRI system offers the ability of imaging organs in a variety of different body positions from horizontal to vertical, thus giving the physicians advantages in diagnosing, as they can compare images of an organ in a few positions. Applicants invention is drawn to such a unique system which will offer benefits associated with imaging organs in more than one position

BRIEF DESCRIPTION OF INVENTION

According to the present invention, an improved magnetic resonance imaging (MRI) system, enabling imaging a variety of organs in several positions of a patient being imaged, said positions ranging form horizontal to vertical is provided; said system comprising:

image data acquisition and processing devices to provide images of the organs, apparatus for displaying the provided images, a rotation mechanism for varying the positions of the subject.

said image acquisition and processing devices including:

a magnet for creating a homogeneous magnetic field in a predetermined volume to align spins in the subject with the magnetic field.

gradient coils for generating gradient fields, a patient's bed for positioning the patient in the magnetic field in any position from horizontal to vertical, radio frequency (RF) coils for applying pulses of electromagnetic radiation to a patient to tip the spins out of alignment; and said rotation mechanism rotating said magnet, said gradient coils, said RF coils and said bed for imaging the patient at any angle.

In one preferred embodiment magnetic shielding is provided for the system, said shielding includes an iron room which provides shielding for the MRI system as well as support for the rotating mechanism.

One advantage of the inventive system is that providing a whole unitary shielding room provides better shielding of the MRI system compared to prior art shielding. Yet another advantage of such a system is it's ability to image any organ in any position between vertical and prone, i.e. any organ can be imaged at a variety spectrum of angles at least between between 0 and 90 degrees, thus providing important diagnostic advantages.

BRIEF DESCRIPTION OF THE DRAWINGS

The above described and other objects and features of the present invention will be best understood when considered in the light of the following description made in conjunction with the accompanying drawings; wherein.

GENERAL DESCRIPTION

The herein described unique MRI system offers several new and inventive features which other existing MRI cannot provide. The unique MRI system enables rotating the data acquisition apparatus together with the patient's bed, thus enabling imaging different organs at as many different angles as desired. Since many organs and body functions have different parameters in different angles, the ability to image organs and body functions at several different angles provides great diagnostic benefits.

Figure 1:
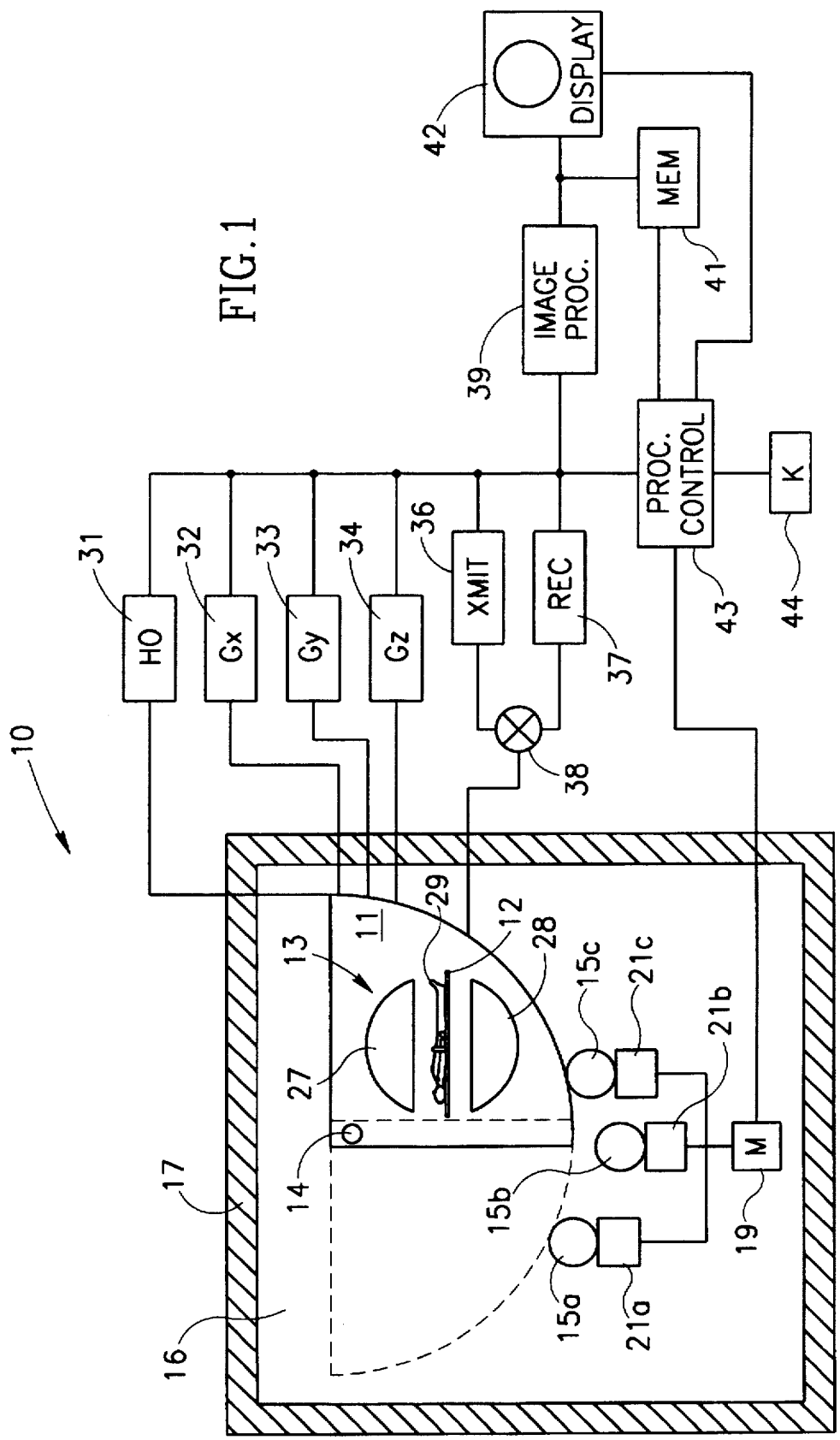
FIG. 1 is a block diagram showing of the inventive MRI system enabling imaging subjects in positions varying at least from standing to prone.

The MRI system of FIG. 1 comprises a quadrant shaped wall unit 11. A magnet 13 is attached to the quadrant shaped wall unit. The magnet is preferably an open magnet comprised of two halves 27 and 28. A patient bed 12 is attached between the magnet halves The entire quadrant with the magnets, gradient coils (not shown) radio frequency (RF) coils (not shown) and the bed 12 rotate with the quadrant 11 about a bearing 14 that attaches the quadrant to a wall 16 of the ferromagnetic room 17 that encloses the MRI system 10. A motor 19 drives drive wheels 15a, 15b, 15c through gear drive units 21a, 21b and 21c to rotate the quadrant shaped wall unit to any desired position of patient 29 ranging at least from lying down to erect.

The magnet coils are energized through magnetic generator unit 31. Gradient coil current generators 32, 33 and 34 are used to activate the gradient coils (not shown). An RF generator transmitter 36 causes the RF coil (not shown) to be energized. A receiver 37 receives signals from the RF coils through multiplexing switch arrangement 38, which controls the transmission of RF pulses and the receipt of free induction decay (FID) signals. The FID signals are processed in image processor 39 which converts the received signals to image data using memory 41. The image data is used to provide images on display monitor 42. All of the MRI system is under the control of control processor 43. Input commands are fed into the processor 43 through an input device such as keyboard 44.

Figure 2:
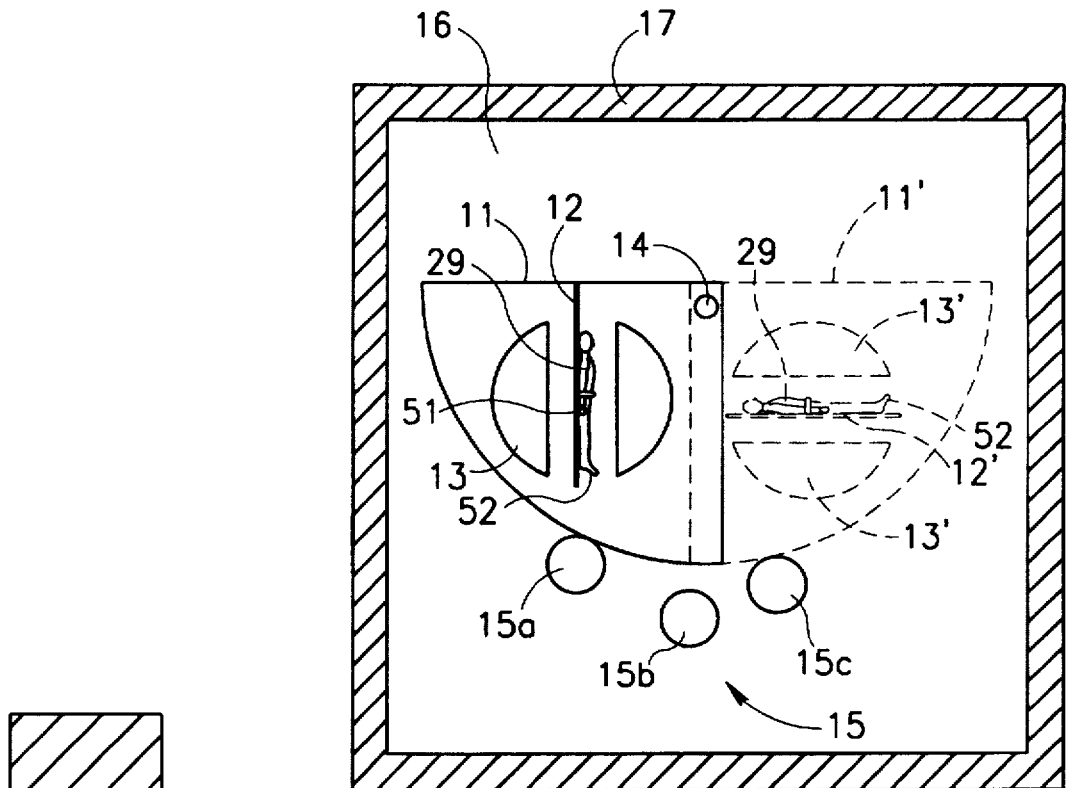
FIG. 2 is a cross sectional view of a portion of a preferred embodiment of the invention.

FIG. 2 is an example of one embodiment of the present invention. The iron quadrant 11, which is part of the MRI system 10, is connected using the bearing rod 14 to a wall 16 of the room 17 occupied by the MRI system. The bearing 14 enables the quadrant 11 to rotate at substantially any angle, at least between 0–90 degrees. A mechanism which includes several wheels 15a, 15b, 15c which are activated by the motor 19 helps to rotate the quadrant to any desired angle, at least between 0–90 degrees. The wheels 15 may be gear wheels with gear teeth on the quadrant or have other means for increasing friction between the wheels and the quadrant. The quadrant before rotation is indicated by the dotted line and referred to as 11'. The image acquisition apparatus 13' comprising a magnet, gradient coils, RF coils, transmitting and receiving equipment and the bed 12' are permanently connected to the quadrant 11'. Thus, when the quadrant rotates the bed and the data acquisition apparatus rotate with it. The position of the data acquisition apparatus and the bed, after the quadrant is rotated through an angle of 90 degrees, is indicated by the solid lines and referred to as 13 and 12, respectively.

Note that the patient 29 may be strapped to the bed 12 using harness 51. A foot platform 52 is provided to help support the patient during the examination in the erect position.

One preferred embodiment of the invention includes the ferromagnetic room 17 for shielding the MRI system from the rest of the world.

Such shielding has many advantages compared to the conventional shields which use a ferromagnetic shielding (usually iron) which is placed around MRI magnet in form of a return yoke. One advantage of the room shielding is that it provides improved shielding, i.e. smaller leakage from the magnetic field to the outside and vice-versa from the outside world to the magnetic field used in the MRI system. A synergistic advantage of using a ferromagnetic room is that it provides excellent support for the rotating MRI system It should be noted that the presence of a ferromagnetic room (usually iron or steel) and a ferromagnetic quadrant should be considered and must be taken into consideration when designing the whole system for maximum magnetic homogeneity as required in MRI imaging systems.

Figure 3:
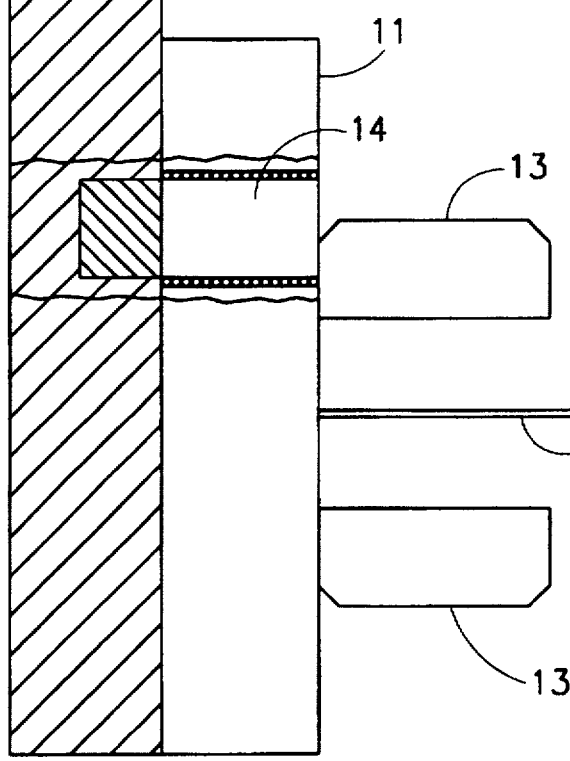
FIG. 3 is a side view of a preferred embodiment of the invention.

FIG. 3 is a side view of the preferred embodiment shown in FIG. 1. The quadrant 11 is connected to the a wall 16 using a bearing 14. The imaging apparatus 13 and the patients bed 12 are permanently connected to the quadrant so they are rotated when the quadrant itself is rotated, thus providing images of an of an organ at more than one position.

The data acquisition apparatus 13, can include any type of magnet used for generating magnetic fields in MRI systems: a permanent magnet, a resistive coil magnet, or a superconducting magnet.

In one preferred embodiment the data acquisition apparatus includes a permanent magnet which can be either a C shaped magnet or an H shaped magnet.

While the invention has been described with reference to a preferred embodiment, it should be understood that this embodiment is exemplary only and is not meant to act as a limitation on the scope of the invention.

We claim:

1. A method for imaging using a magnetic resonance imaging (MRI) system, said MRI imaging system including a magnet;

said method including:

rotating said magnet and a patient's support that supports a patient, while acquiring MRI images to provide images of a variety of organs in different postures;

creating a homogeneous magnetic field in a predetermined volume that includes said patient's support;

generating gradient fields in the predetermined volume;

generating radio frequency pulses for applying said pulses to a patient supported on said patient's support;

wherein rotating said magnet and said patient's support includes rotating said magnet and said paient's support within a ferromagnetic room and relative to the room.

arranging said magnet to have a first half and second half each of said first half and said second half extending along the length of said patient and said magnet being oriented with said first half above and said second half being below said patient when said patient's support is rotated to support the patient in a supine position and with said first half being positioned along a backside and said second half being positioned along a front side of said patient when said patient's support is rotated to support the patient in an erect position.

2. The method of claim 1 wherein said step of creating a homogeneous magnetic field includes using a superconducting magnet.

3. The method of claim 1 wherein said step of creating a homogeneous magnetic field includes using a resistive coil magnet.

4. The method of claim 1 wherein said step of creating a homogeneous magnetic field includes using a permanent magnet.

5. The method of claim 1 wherein the step of rotating said magnet and said patient's support includes the step of rotating a quadrant, connecting said quadrant to a wall of said ferromagnetic room with a bearing, also connecting said quadrant to said magnet and said patient's support, and said step of rotating said quadrant enabling rotation of said magnet and said patient's support at any angle.

6. A method for magnetic resonance imaging (MRI), said method including:

rotating an MRI system including a magnet and a patient's bed while acquiring MRI images to provide images of a variety of organs in different postures;

creating a homogeneous magnetic field in a predetermined volume;

generating gradient fields;

shielding said MRI system and said patient's bed;

creating radio frequency (RF) pulses;

applying said RF pulses to a patient lying on said patient's bed;

said shielding including enclosing said MRI system in a ferromagnetic room; and rotating said MRI system and said patient's bed to enable said MRI system and said patient's bed to rotate at any angle.

7. The method of claim 6 wherein said step of rotating said MRI system and said patient's bed includes using a ferromagnetic quadrant which is connected to a wall of said ferromagnetic room with a bearing and to said MRI system and said patient's bed, said ferromagnetic quadrant enabling rotation of the patient at any angle.

* * * * *